US009447405B2

United States Patent
Johnson et al.

(10) Patent No.: US 9,447,405 B2
(45) Date of Patent: Sep. 20, 2016

(54) REGULATION OF SPECIFIC SPINAL NEURONS REGULATING PAIN TRANSMISSION VIA CHIMERIC TOXINS

(71) Applicants: Eric A. Johnson, Madison, WI (US); Sabine Pellett, Madison, WI (US); William H. Tepp, Stoughton, WI (US); Tony L. Yaksh, San Diego, CA (US); Marc Marino, San Diego, CA (US); Qinghao Xu, San Diego, CA (US)

(72) Inventors: Eric A. Johnson, Madison, WI (US); Sabine Pellett, Madison, WI (US); William H. Tepp, Stoughton, WI (US); Tony L. Yaksh, San Diego, CA (US); Marc Marino, San Diego, CA (US); Qinghao Xu, San Diego, CA (US)

(73) Assignees: WISCONSIN ALUMNI RESEARCH FOUNDATION, Madison, WI (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 83 days.

(21) Appl. No.: 14/181,241

(22) Filed: Feb. 14, 2014

(65) Prior Publication Data
US 2014/0255376 A1    Sep. 11, 2014

Related U.S. Application Data

(60) Provisional application No. 61/775,116, filed on Mar. 8, 2013.

(51) Int. Cl.
| | |
|---|---|
| A61K 38/16 | (2006.01) |
| A61K 39/08 | (2006.01) |
| C07K 14/33 | (2006.01) |
| C12N 9/96 | (2006.01) |
| C07K 7/22 | (2006.01) |
| A61K 47/48 | (2006.01) |
| C07K 14/575 | (2006.01) |
| C07K 14/70 | (2006.01) |
| C07K 14/72 | (2006.01) |
| A61K 38/48 | (2006.01) |

(52) U.S. Cl.
CPC .............. *C12N 9/96* (2013.01); *A61K 38/164* (2013.01); *A61K 38/4893* (2013.01); *A61K 47/48238* (2013.01); *C07K 7/22* (2013.01); *C07K 14/33* (2013.01); *C07K 14/57545* (2013.01); *C07K 14/70* (2013.01); *C07K 14/72* (2013.01); *C07K 2319/01* (2013.01); *C07K 2319/33* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 6,500,436 | B2 | 12/2002 | Donovan |
| 6,641,820 | B1 | 11/2003 | Donovan |
| 7,138,127 | B1 | 11/2006 | Donovan |
| 2003/0165541 | A1 | 9/2003 | Donovan |
| 2006/0216313 | A1 | 9/2006 | Brooks et al. |
| 2009/0220568 | A1 | 9/2009 | Brooks et al. |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Anton, et al., Development of a biotinylated analog of substance P for use as a receptor probe. Lab Invest. May 1991; vol. 64(5): 703-708.
Baldwin, et al., The C-terminus of botulinum neurotoxin type A light chain contributes to solubility, catalysis, and stability. Protein Expr Purif. Sep. 2004; vol. 37(1):187-195.
Belanger, et al., Expression of calcitonin gene-related peptide, substance P and protein kinase C in cultured dorsal root ganglion neurons following chronic exposure to mu, delta and kappa opiates. Neuroscience. 2002, vol. 115 (2):441-53.
Chen, et al., Design of an in vivo cleavable disulfide linker in recombinant fusion proteins. BioTechniques, 2010; vol. 49(1): pp. 513-518.
Huang, et al., Spinal botulinum neurotoxin B: effects on afferent transmitter release and nociceptive processing. PLoS One. Apr. 29, 2011; vol. 6(4):e19126. Erratum in: PLoS One. 2011;6(8).
King, et al., Evolution of key cell signaling and adhesion protein families predates animal origins. Science 2003, vol. 301 (5631): 361-3.
Lappi , et al., Reducing the heterogeneity of chemically conjugated targeted toxins: Homogeneous basic FGF-saporin. Anal Biochem. Aug. 1, 1993; vol. 212(2): 446-451.
G. Mustafa, E.M. Anderson, Y. Bokrand-Donatelli, J.K. Neubert, R.M. Caudle—"Anti-nocieptive effect of a conjugate of substance P and light chain of botulinum neurotoxin Type A" Pain, vol. 154, pp. 2547-2553 (2013), Elsevier B.V.
Todd, et al., Projection neurons in lamina I of rat spinal cord with the neurokinin 1 receptor are selectively innervated by substance p-containing afferents and respond to noxious stimulation. J Neurosci. May 15, 2002; vol. 22 (10):4103-13.
Wiley, et al., Destruction of neurokinin-1 receptor expressing cells in vitro and in vivo using substance P-saporin in rats. Neurosci Lett. Jul. 18, 1997; vol. 230(2): 97-100.
Wiley, et al., Targeted toxins in pain. Adv Drug Deliv Rev. Aug 28, 2003; vol. 55(8): 1043-1054.

(Continued)

*Primary Examiner* — Christine J Saoud
*Assistant Examiner* — Jon M Lockard
(74) *Attorney, Agent, or Firm* — Quarles & Brady LLP

(57) ABSTRACT

A chimeric toxin is disclosed comprising a peptide ligand specifically targeting neurons involved in pain processing; and a clostridial neurotoxin light chain, wherein the ligand is linked to the light chain. The methods of preparing such chimeric toxin and the method of using the chimeric toxin to regulate pain transmission are also disclosed.

4 Claims, 15 Drawing Sheets

(56) References Cited

OTHER PUBLICATIONS

Wiley, et al., Anti-nociceptive effects of selectively destroying substance P receptor-expressing dorsal horn neurons using [Sar9,met(O2)11]-substance P-saporin: Behavioral and anatomical analyses. Neuroscience. May 25, 2007; vol. 146(3): 1333-1345.

Benoliel, et al., Actions of Intrathecal Diphtheria Toxin-Substance P Fusion Protein on Models of Persistent Pain, Pain, 1999, 79:243-253.

Caudle, et al., Central Sensitization in the Trigeminal Nucleus Caudalis Produced by a Conjugate of Substance P and the A Subunit of Cholera Toxin, The Journal of Pain, 2010, 11(9):838-846.

Duggan, et al., Inhibition of Release of Neurotransmitters from Rat Dorsal Root Ganglia by a Novel Conjugate of a Clostridium Botulinum Toxin A Endopeptidase Fragment and Erythrina Cristagalli Lectin, The Journal of Biological Chemistry, 2002, 277(38):34846-34852.

Foster, Engineered Toxins: New Therapeutics, Toxicon, 2009, 54:587-592.

PCT International Search Report and Written Opinion, PCT/US2014/016695, Jun. 23, 2014.

PCT International Preliminary Report on Patentability, PCT/US2014/016695, Sep. 17, 2015.

* cited by examiner

Targeted BoNT-LC

SP-LC:
(SEQ ID NO:2)

Substance P
MLGFFQQPKPRGGGGGGYC-S-S-

BoNT LC

DAMGO-LC:
(SEQ ID NO:3)

DAMGO
H-Tyr-D-Ala-Gly-N-MePhe-Gly-OH-GGGGGGYC-S-S-

REGULATION OF SPECIFIC SPINAL NEURONS REGULATING PAIN TRANSMISSION VIA CHIMERIC TOXINS

CROSS-REFERENCE TO RELATED APPLICATION

This application claims the benefit of U.S. Provisional Patent Application Ser. No. 61/775,116 filed Mar. 8, 2013, incorporated by reference herein.

STATEMENT REGARDING FEDERALLY SPONSORED RESEARCH OR DEVELOPMENT

This invention was made with government support under AI095274 awarded by the National Institutes of Health. The government has certain rights in the invention.

BACKGROUND OF THE INVENTION

Pain generated by peripheral tissue injury leads to the activation of populations of small primary afferents (C fibers), populations of which release substance P (e.g. are peptidergic) and activate second order spinal dorsal horn neurons. This peptide acts on the second order neuron through neurokinin 1 (NK-1) receptors to excite the second order neurons. While other transmitters (such as glutamate) released from the afferent, may play a more important role in exciting the second neurons, the NK1 receptor can be considered to mark the cells, many of which project to the brain, which are playing an important role in pain processing.

It is known that regulating the excitability of the small afferent second order link can produce a powerful and selective analgesia. On example of this is the powerful analgesic action of morphine when given spinally. Because mu opiate receptors (though which morphine acts in spinal cord) are located on many of these peptidergic C fibers, and because the activation of the terminal opiate receptors blocks the opening of voltage sensitive calcium channels, this presynaptic effect serves to block transmitter release from only these C fiber terminals. As these opiate receptors are located only on small afferents, the release of transmitters from other sensory axons, which are often non nociceptive (e.g. mediates for example light touch), are not affected. Spinal opiates affect pain, but not non-painful sensation. In addition, it is known that there are opiate receptors which are on second order neurons and the activation of these neurons by noxious input can be reduced by the agonist occupancy of these post synaptic opiate receptors.

The above commentary emphasizes the role of the NK1 receptor as marking cells which are post synaptic to pain fibers on mu opioid receptors present on spinal C fiber (pain fiber) terminals, and on second order neurons which are carrying pain information. This organization is illustrated in FIG. 1.

An important property of these NK1 and mu opioid receptors is that they are G protein coupled receptors. When their respective agonists occupy them they will internalize the bound agonists into the cell.

It has been shown that this internalization process can be used to target specific cell to take up large proteins. One well-known example is the saporin complex. Coupling this 31 kDa toxin to sP will cause that toxin to be taken up into neurons, which are expressing NK1 receptors. Upon binding, this complex internalizes into the cell (and only that cell with an NK1 receptor), where upon the toxin will kill that cell. Studies with the intrathecal delivery of substance P-Saporin have shown a prominent analgesia after such treatment reflecting the importance of these important NK1 bearing neurons in pain processing. This strategy is by its nature results in permanent and irreversible neuron loss. Such therapy would be limited to those patients with terminals illnesses. Therefore, there is a critical need to develop a new therapy that can be applicable to the vast majority of pain patients suffering from chronic pains, such as, for example, musculoskeletal and low back pain.

SUMMARY OF THE INVENTION

The present invention can be broadly summarized as a chimeric toxin for regulating the pain transmission, methods of preparing the chimeric toxin, and methods of using the chimeric toxin to treat pain. In one embodiment, the regulation is long-lasting and/or stable and/or reversible.

In its first aspect, the present invention is directed to a chimeric toxin comprising (a) a peptide ligand specifically targeting neurons involved in pain processing; and (b) a clostridial neurotoxin light chain, wherein the ligand is linked to the light chain to form a chimeric toxin and wherein the chimeric toxin does not comprise a translocation domain.

In one embodiment, the ligand of the chimeric toxin is a ligand for neuronal GPCR. Preferably, the GPCR is selected from the group consisting of Substance P, DAMGO, NPY, Dexmed, GPR, derivatives thereof and mixtures thereof. More preferably, the GPCR is Substance P or DAMGO.

In one embodiment, the light chain is a light chain of clostridial neurotoxin or *botulinum* toxin selected from the group consisting of type A, type B, type C, type D, type E, type F, type G, tetanus, and the subtypes or mixtures thereof. Preferably, the light chain is *botulinum* toxin type A light chain, or *botulinum* toxin type B light chain.

In one embodiment, the light chain and the ligand are linked through a covalent bond. Preferably, the covalent bond comprises a disulfide linker.

In its second aspect, the present invention is directed to methods of preparing the chimeric described above.

In one embodiment, the method of preparing the chimeric toxin comprises the step of linking a clostridial neurotoxin light chain to a peptide ligand specifically targeting neurons involved in pain processing, wherein the chimeric toxin does not comprise a translocation domain.

In one embodiment, the method of preparing the chimeric toxin comprises the step of linking a clostridial neurotoxin light chain to a peptide ligand specifically targeting neurons involved in pain processing, wherein the light chain is linked to the ligand by recombinant synthesis in *E. coli.*, and wherein the chimeric toxin does not comprise a translocation domain.

In one embodiment, the method of preparing the chimeric toxin capable of regulating pain transmission comprises the step of linking a clostridial neurotoxin light chain to a peptide ligand specifically targeting neurons involved in pain processing, wherein the light chain is expressed in *E. coli* in a truncated form, and wherein the chimeric toxin does not comprise a translocation domain.

In one embodiment, the method of preparing the chimeric toxin capable of regulating pain transmission comprises the step of linking a clostridial neurotoxin light chain to a peptide ligand specifically targeting neurons involved in pain processing, wherein the light chain is expressed in *E. coli* in an extended version of the truncated form including a C-terminal cysteine, and wherein the chimeric toxin does not comprise a translocation domain.

In one embodiment, the method of preparing the chimeric toxin capable of regulating pain transmission comprises the step of linking a clostridial neurotoxin light chain to a peptide ligand specifically targeting neurons involved in pain processing, wherein the full length of the clostridial neurotoxin light chain is expressed in *E. coli*. Preferably, the full length light chain comprises a naturally occurring cysteine. More preferably, the full length light chain comprises both naturally occurring cysteines and the trypsin cleavage site, and wherein the chimeric toxin does not comprise a translocation domain.

In one embodiment, the method of preparing the chimeric toxin capable of regulating pain transmission comprises the step of linking a clostridial neurotoxin light chain to a peptide ligand specifically targeting neurons involved in pain processing, wherein the light chain is expressed in *E. coli* in an extended version of the truncated form including an enzyme-cleavable disulfide linker, and wherein the chimeric toxin does not comprise a translocation domain.

In another embodiment, the method of preparing the chimeric toxin capable of regulating pain transmission comprising the step of linking a clostridial neurotoxin light chain to a peptide ligand specifically targeting neurons involved in pain processing, wherein the light chain is expressed in *E. coli* in an extended version comprising at least aa 454 (cysteine), and wherein the chimeric toxin does not comprise a translocation domain. Preferably, the light chain is fused to the sequence encoding for the ligand.

In some embodiments, the methods of preparing the chimeric toxin comprises the step of linking the light chain to the ligand through a disulfide linker.

In some embodiments, the ligand is produced synthetically.

In some embodiments, the ligand is produced synthetically with modifications that include adding a linker and a cysteine such that disulfide bonding can occur.

In its third aspect, the present invention provides a method for regulating pain transmission in a patient, the method comprising the step of administrating a formulation comprising an effective amount of the chimeric toxin described above.

In one embodiment, the formulation may comprises a therapeutically effective amount of the chimeric toxin and a pharmaceutically acceptable carrier.

In one embodiment, the formulation is delivered into lumbar intrathecal puncture space. Preferably, the formulation is delivered in a water based isotonic vehicle prepared freshly prior to the administration. Preferably, the formulation is delivered in an effective amount in the range of 5 to 500 U typically delivered in a volume of 1 mL. In another embodiment, the formulation is delivered in an effective amount in the range of 0.005 to 50 micrograms. Preferably, the formulation is delivered in an effective amount of 0.5 micrograms.

In one embodiment, the pain that can be treated by the described method arises from cutaneous injury and inflammation, musculoskeletal injury and inflammation, visceral inflammation or injury, peripheral nerve injury as caused by chemicals, metabolic disease, physical injury, and mixtures thereof.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 2 is a schematic showing the proposed target LC (light chain) derivatives of the LC of a BoNT linked to the N-terminus of substance P (SEQ ID NO: 2) or the C-terminus of DAMGO (SEQ ID NO: 3) through a disulfide linkage. Other strategies will include addition of a portion of the HC associated with translocation.

FIG. 5A-C displays the biphasic flinching evoked over 60 min by intraplantar formalin in 4 control mice. A. Formalin evoked flinching (flinches/min: mean±SEM) assessed in animals receiving intrathecal vehicle (N=4, mean±SEM) or B. IT sP-LC (0.55 µg/10 µL) (N=2), 24 hrs prior to formalin assessment. C. Figure presents the cumulative phase 1 and phase 2 flinching scores for the 60 min test interval for each mouse. As noted, phase 2 flinching scores of the mice receiving the IT-sP-LC were less than 50% of the control animal flinching scores.

DESCRIPTION OF THE INVENTION

Figure 1:
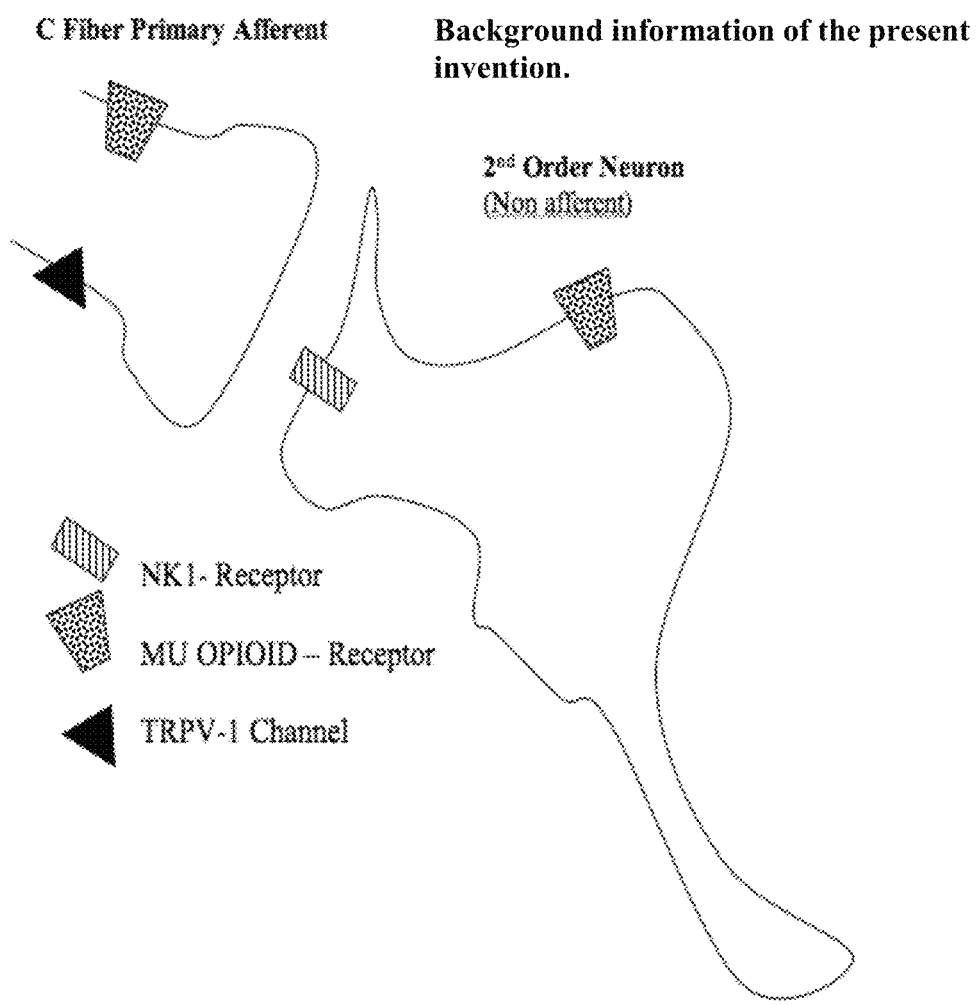
FIG. 1 is a schematic showing 1° order neurons (primary afferent C fiber) which is peptidergic (substance P positive) and $2^{nd}$ order neuron in spinal dorsal horn showing the pre/post synaptic location of NK1, Mu and TRPV1 receptors. This figure is provided for the purpose of demonstrating background information of pain transmission.
Figure 3A:
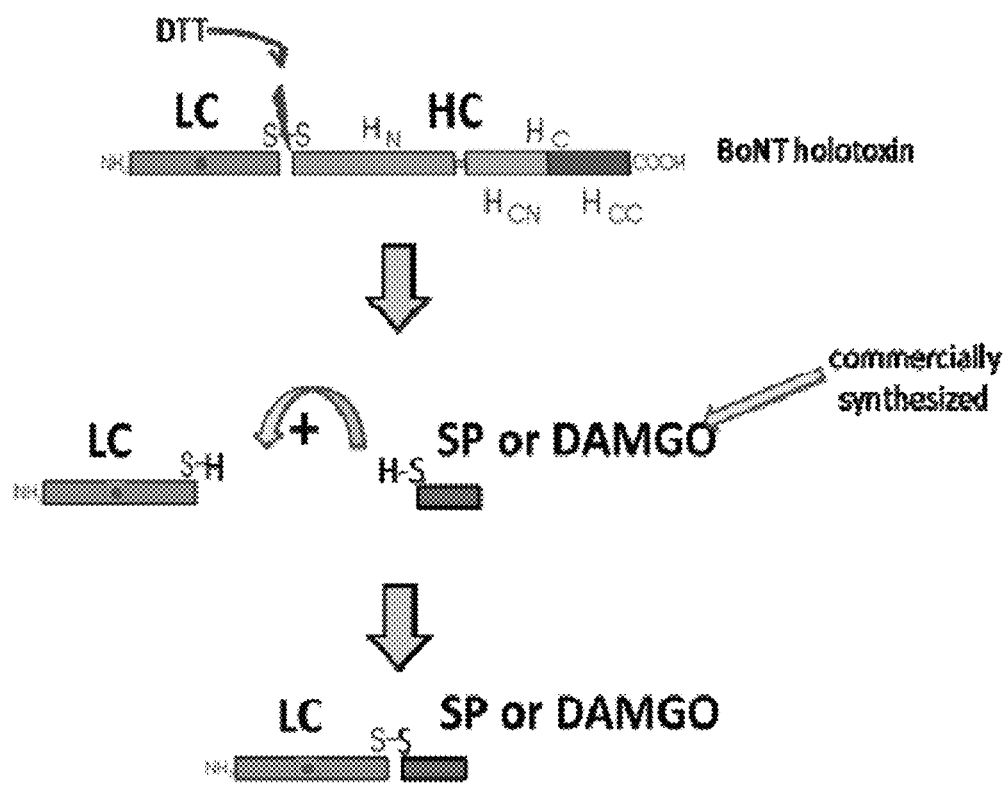
FIG. 3A-G is a schematic showing the proposed approaches for constructing the LC (light chain) or its derivatives to substance P (sP) or DAMGO. A. The first method of creating sP-LC/DAMGO-LC construction; B. The second method of creating sP-LC/DAMGO-LC construction; C. The third method of creating sP-LC/DAMGO-LC construction; D. The fourth method of creating sP-LC/DAMGO-LC construction; E. The fifth method of creating sP-LC/DAMGO-LC construction; F. The sixth method of creating sP-LC/DAMGO-LC construction; G. The seventh method of creating sP-LC/DAMGO-LC construction.
Figure 3B:
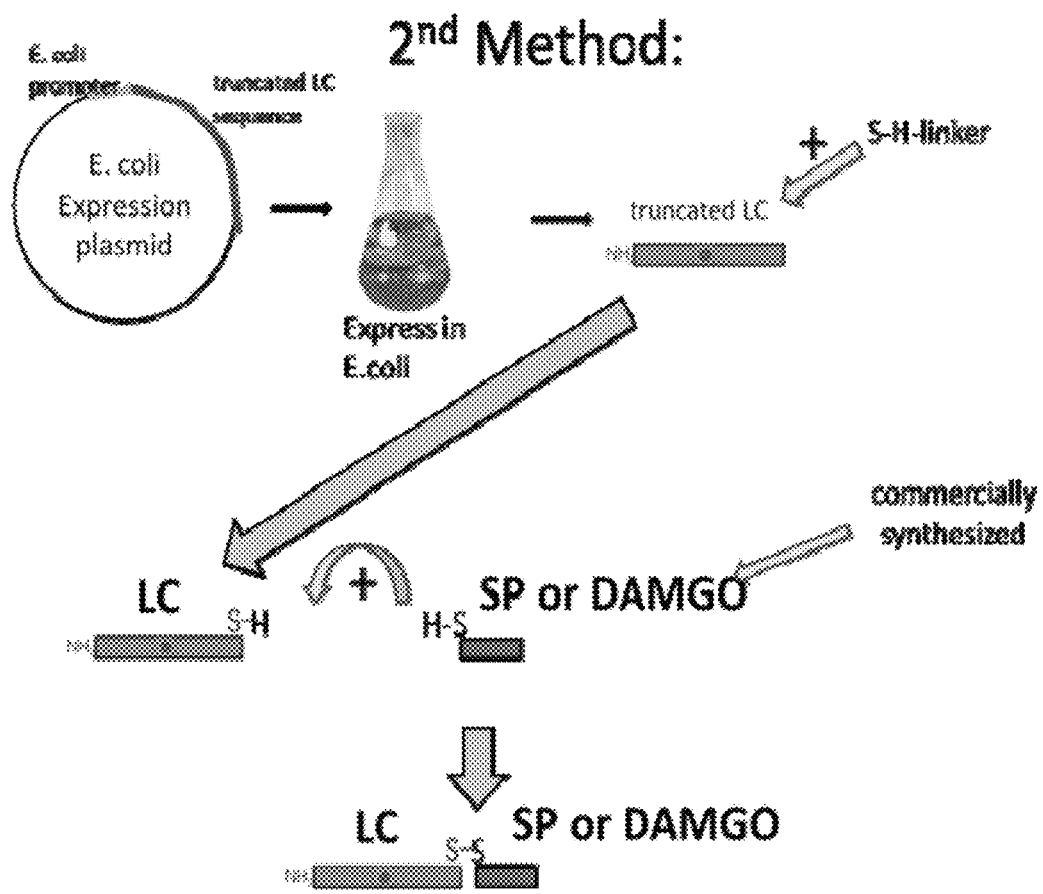
Figure 3C:
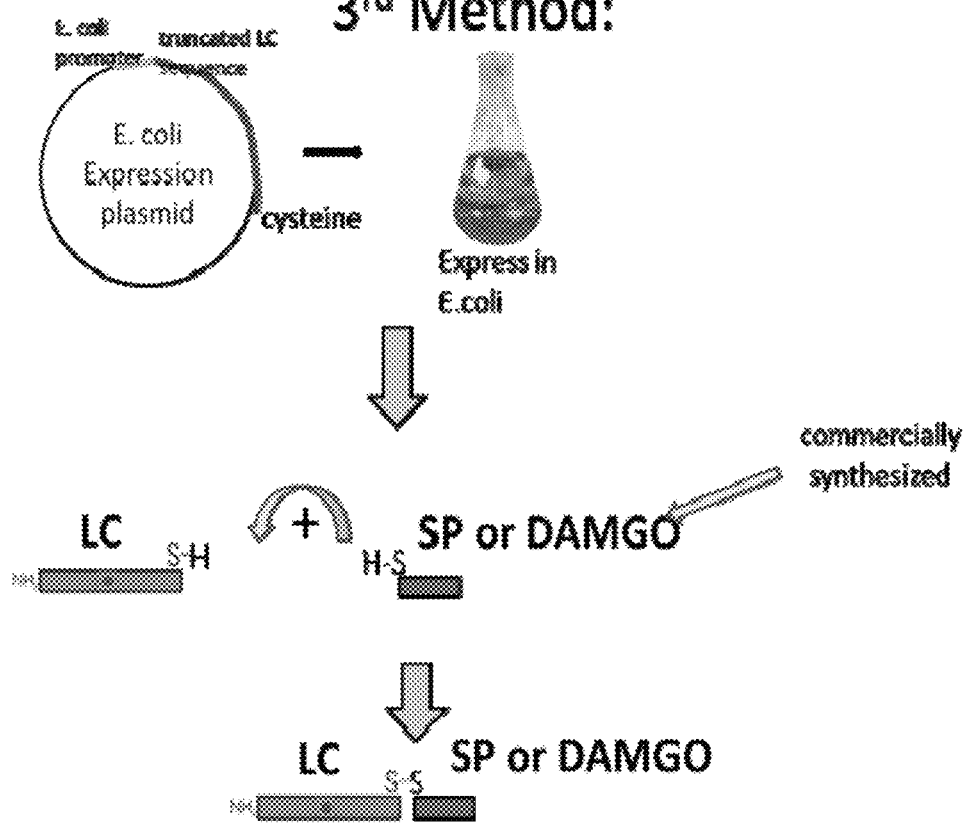
Figure 3D:
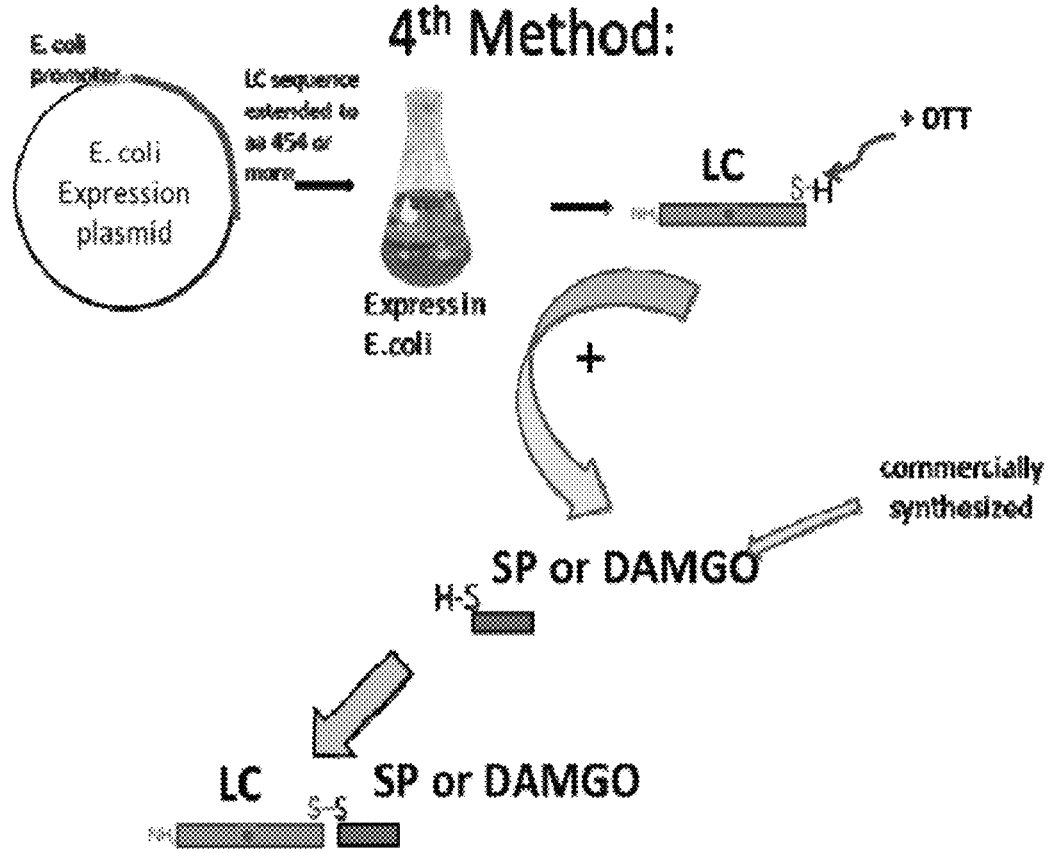
Figure 3E:
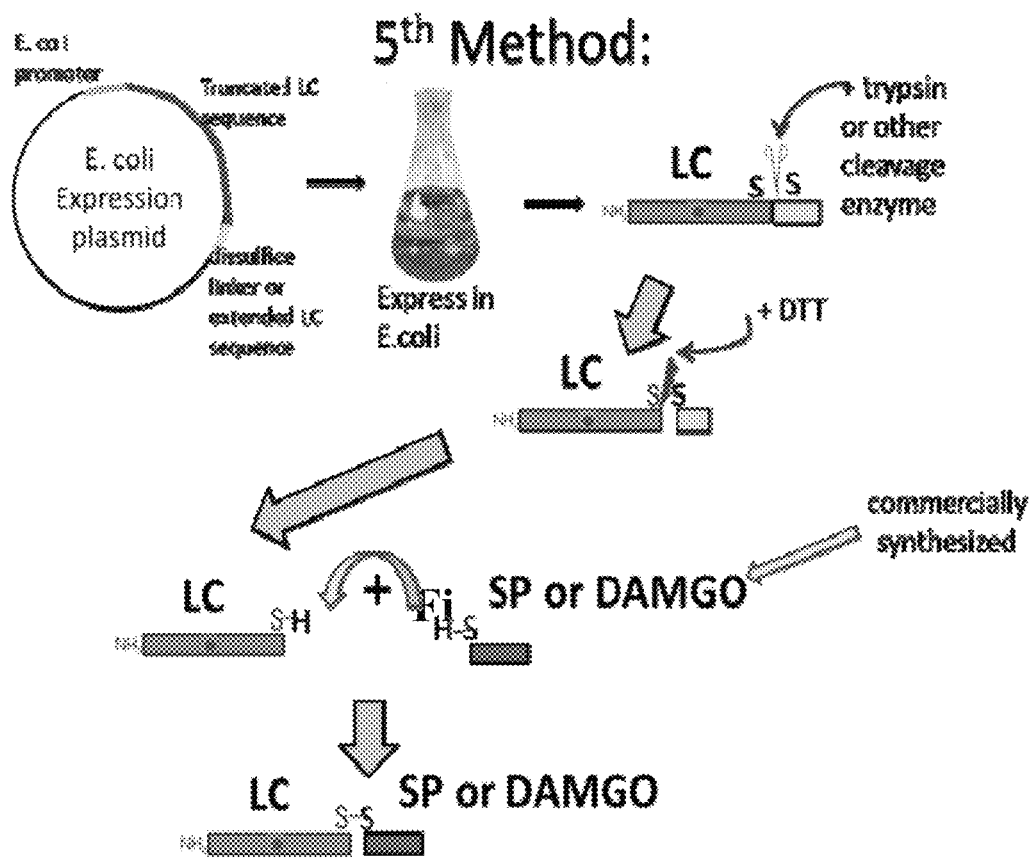
Figure 3F:
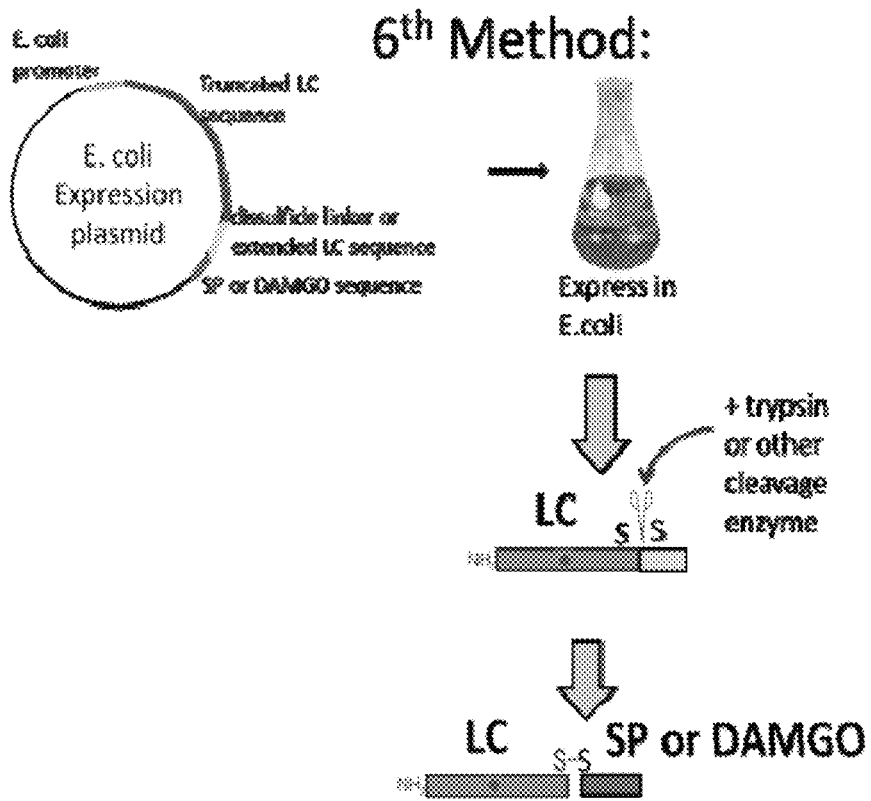
Figure 3G:
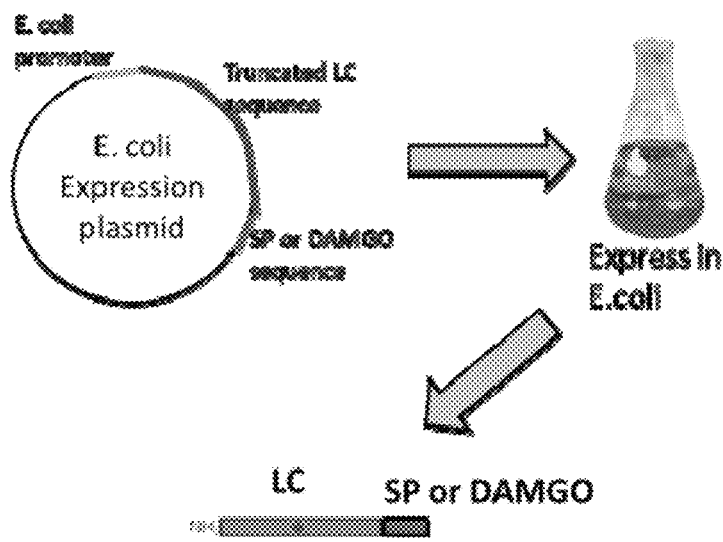

The present invention provides an alternate strategy for regulating pain transmission. This strategy is based on the use of agents to prevent the release of terminal transmitters by cleaving synaptic protein. One such class of agents is clostridial neurotoxin or *botulinum* toxins (BoNTs). *Botulinum* toxins are zinc proteases constituted of several components including a heavy chain (HC), which serves to assist the toxin in being taken up by the cell and is connected by disulfide linkages to a light chain (LC), which after being taken up and freed from its HC components serves to cleave specific synaptic proteins.

The cleavage results in two events. The first is the well known prevention of release of neurotransmitters such as glutamate and substance P (sP) which are known to be important in spinal pain transmission. The second is that these synaptic proteins also are essential in the membrane trafficking of excitatory receptors that are believed to play a role in spinal pain processing. These vents are blocked until such time as the toxin is degraded and new functional synaptic protein is synthesized.

We have recently shown that after spinal delivery, one such toxin (BoNT/B) will indeed block release of sP from C fibers and produce a persistent antinociception (Huang, et al, 2011). However, a limitation of this BoNT approach is that the uptake mechanisms for the BoNTs are not selective and up-take may occur into many cells including those which are non primary afferent, many of which may be inhibitory. This leads to a dilemma wherein the spinal effects may lead to untoward actions, including enhanced pain.

Thus, a toxin comprising only the LC is a solution to this dilemma. However, the challenge is that while the LC is enzymatically active, it is not able to be taken up by any cell. In the present invention, we have solved this problem by coupling the LC to a ligand, wherein the ligand has the function of carrying any coupled molecule into cells. One of the advantages of this strategy is that only the enzymatically active LC can be delivered into cells with an appropriate receptor, and once inside the cell, the LC is separated from the ligand and is able to cleave targeted proteins.

In its first aspect, the present invention is directed to a chimeric toxin comprising (i) a peptide ligand specifically targeting neurons involved in pain processing; and (ii) a clostridial neurotoxin light chain, wherein the ligand is linked to the light chain and, and wherein the chimeric toxin does not comprise a translocation domain.

A "light chain" means the light chain of a clostridial neurotoxin. In some cases, a light chain has a molecular weight of about 50 kDa or smaller, and can be referred to as light chain, LC or proteolytic domain of a clostridial neurotoxin. A light chain also means a protein or peptide that retains cleavage activities that attacks fusion proteins, such as SNARE, SNAP-25, syntaxin or synaptobrevin.

In some embodiment, the clostridial toxin light chain of the present invention can be, for example, wild type and non-naturally occurring forms of *botulinum* toxin light chain type A, type B, type C, type D, type E, type F or type G or tetanus toxin (TeNT) light chain, or their subtypes, and mixtures thereof.

The sequence of a clostridial toxin light chain can be determined based on a desired altered protease specificity or other enzymatic properties desired in the light chain. Clostridial toxin light chains include wild type clostridial toxin light chains as isolated from any serotype of *Clostridia* as well as mutant or modified clostridial toxin light chains that differ from a wild type clostridial toxin light chain by one or more amino acids and have a useful characteristic.

The nucleic acid and corresponding amino acid sequences for wild type clostridial toxins or their light chains are also well known in the art. For example, in one embodiment of the invention, one would prepare *botulinum* neurotoxin light chain type A (LC/A) by obtaining a DNA sequence encoding LC/A and deleting the C-terminal portion of the sequence so that the nucleic acid sequence encodes amino acid residues 1 through 419-447. Preferably, the light chain is a truncated light chain having amino acid residues 1 through 425 (aa 1-425).

However, one skilled in the art understands that, due to the degeneracy of the genetic code, a variety of different nucleic acid sequences encoding the same or similar amino acid sequences or a functional fragment thereof can be used as well. For example, the clostridial toxin light chain can differ from a naturally occurring clostridial toxin light chain by one or more amino acid substitutions, and, in one embodiment, differs from a naturally occurring clostridial toxin light chain by at most three amino acid substitutions. In another embodiment, the encoded evolved clostridial toxin light chain differs from a naturally occurring clostridial toxin light chain by one or more, but at most three amino acid substitutions. For example, a fragment comprising residues 1-424 or 1-426 is also considered as a sequence consisting essentially of residues aa 1-425 of BoNT type A. However, in no embodiment does the light chain of the present invention include a nucleic acid sequence encoding a clostridial toxin heavy chain.

In some embodiments, the light chain also can be a native light chain, a truncated light chain, a fragment of a light chain, or a modified light chain, as long as it possesses some or all of the biological activities of a native light chain in accordance with the present invention. Preferably, this biological activity would be protease or cleavage activity.

In a preferred embodiment, the light chain used for forming the chimeric toxin of the present invention does not contain or is not linked to a translocation domain derived from a heavy chain. Translocation domain is part of a heavy chain that facilitates the translocation of the light chain to the cytoplasmic compartment.

One would also appreciate that any ligand targeting neurons involved in the transmission, modulation and sensation of pain may be coupled with a light chain for carrying out the purpose of the present invention. Selection of the ligands may be based on their affinity for specific neuron receptors. For example, one such class of ligands is the neuronal G protein-coupled receptors (GPCR) or their subunits that are known to be involved in pain processing (King, et al., 2003). The examples of GRCR include, but not limited to Substance P, DAMGO, NPY, Dexmed and GPR (Belanger, et al, 2002) or their derivatives. The term "derivative" refers to any compound or molecule which is derived or modified from a GPCR and exhibits equal or similar levels of biological activity as a natural GPCR.

In a particular embodiment, the ligand is substance P (peptide RPKPQQFFGLM, SEQ ID NO:1), which is an agonist of the neurokinin-1 receptor (NK1 receptor), or DAMGO, which is an agonist of the mu opioid receptor.

The light chain and the ligand can be obtained by other methods known in the art. For example, either of them can be obtained by chemical synthesis or produced in a host organism such as bacteria with the use of recombinant technology. For example, a light chain is most easily obtained by recombinant expression in a host organism such as E. coli. The light chain and ligand are also commercially available. The entire construct of the light chain and the ligand can be expressed as one recombinant protein in a host.

After one has obtained both the light chain and the ligand, one must link the light chain and the ligand together with retention of biological activity. Thus, in its second aspect, the present invention is directed to methods of preparing a chimeric toxin by linking the LC with a ligand specifically targeting neurons involved in pain processing, wherein the chimeric toxin does not comprise a translocation domain.

It should be noted that the LC can be linked to the ligand by any technologies known in the art, as long as their biological activities are retained. FIG. 3 and the following examples provide several preferred approaches to construct the chimeric toxin and the preferable linkers.

For example, the linking can be accomplished by forming a covalent bond between two reactive functional groups or moieties. The linking can also be done by use of a coupling reagent, which promotes reaction of two reactive functional groups with each other to form a direct bond. The coupling agent can be a cross-linking reagent, which modifies at least one of the functional groups and results in the incorporation of a bridging moiety between the molecules.

The location of the link can be in any part of the chimeric toxin. In a preferred embodiment, the link is located in the carboxyl terminus, leaving the amino terminus essential for binding intact. Such location has several advantages. First, the binding at this location can promote the chimeric toxin to be internalized into cells through G protein receptor. Second, once inside the local environment of a cell, acidification will free the light chain by cleavage of the disulfide linkage. Third, the enzymatic activity of *botulinum* toxins for the synaptic protein is limited to the light chain and its action will lead to block of transmitter release from that terminal. Another significant benefit of this embodiment is that the coupling to the light chain prevents the targeting and cargo complex to be taken up by any cell not possessing the appropriate cell surface markers.

In some embodiments, the light chain and the ligand are connected by a covalent bond. The preferred strategy to create such covalent bond is through building a disulfide bond between the light chain and the ligand.

For example, in a specific embodiment, the targeting ligand (such as sP or DAMGO) is produced synthetically and linked to the LC via disulfide bond. For this, the LC can be either expressed in E. coli as the more stable truncated form (Balwin, et al., 2004) or an extended version of the truncated form including either a C-terminal cysteine or an enzyme-cleavable disulfide linker (Chen, et al., 2010).

In some embodiments, the full length LC including the naturally occurring cysteines is expressed in E. coli and used instead. It is also envisioned that an extended version including both naturally occurring cysteines and trypsin cleavage sites would work as well. In either way, the ligand will be synthesized with modifications that include an additional cysteine such that disulfide bonding to the LC at a specific protein site via disulfide bonding.

In some embodiments, the LC is expressed in E. coli either as the truncated form (no longer than 425 amino acids), or fragments thereof that retain SNARE cleavage activity, or as the extended LC having at least 454 amino acids with aa 454 (cys), then the LC is fused to the sequence encoding for the ligand via a disulfide linker (Chen, et al., 2010). The subsequent purification and thrombin (or other enzyme) cleavage can be performed as described in Baldwin, et al., 2004 and Chen, et al., 2010.

In some embodiments, the BoNT-LC is coupled to a targeting ligand by chemical synthesis. Preferably, the chemical synthesis is accomplished by using one of the following approaches. The first approach is that the LC is derivatized with N-succinimidyl-3-[2-pyridyldithio]propionate (SPDP), in which the mono-derivatized LC may be selected as described in Lappi, et al., 1993. Then the modified ligands, such as sP or DAMGO peptides containing a cysteine at the C-terminal end and a 6-glycine linker are added to the LC derivative to allow for conjugation.

The second approach starts with the LC, which is constructed to contain the cysteine 430 at the C-terminus. The LC construct then is treated with a reducing agent such as dithiothreitol to break up dimers, and dialyzed into a buffer that will maintain the free sulfhydryl group of the cysteine. One example of the buffer is 1-10 mM (ethylenedinitrilo)-tetraacetic acid. Next, the LC construct is reacted with sP or DAMGO constructs containing a cysteine or a cysteine modified with a pyridyl thione group at the N-terminal end.

After the construction, one could identify the resulting chimeric toxin and assess the bioactivities thereof by any technologies known in the art. For example, one would use SDS-PAGE gel and immunoblot analyses, alongside BoNT holotoxin to identify the chimeric toxin. One would assess the purity of the chimeric toxin by SDS-PAGE analysis and confirm the absence of toxicity by mouse bioassay (Schantz and Kautter, 1978; Hatheway, et al., 1988). One would confirm the LC activity by in vitro endopeptidase assays (BoTest; Biosentinel, Madison, Wis.). One would also wish to treat the resulting chimeric toxin with a reducing agent such as dithiothreitol to achieve full function of the LC.

In its third aspect, the present invention is directed to a method for regulating pain transmission in a patient, the method comprising the step of administrating a formulation comprising an effective amount of the chimeric toxin as described above.

The chimeric toxin may be administered in any suitable formulation. The formulation may be produced using any suitable technique known in the art. For example, prior to administration, the chimeric toxin is suspended in a suitable vehicle for injection. Preferably, the formulation is delivered in a water-based isotonic vehicle freshly prepared prior to the administration. The water-based isotonic vehicle may contain pharmaceutical excipients such as mannitol, sodium chloride, glucose, dextrose, sucrose, or glycerins, non-ionic surfactants (e.g., poloxamers, poly(oxyethylene)-sorbitan-fatty acid esters, carboxymethyl cellulose sodium (CMC-Na), sorbitol, poly(vinylpyrrolidone), or aluminium monostearate in order to ensure a suitable isotonicity.

The formulation should comprise an effective amount of the chimeric toxin of the present invention. An effective amount is at least the minimal amount of the chimeric toxin or a pharmaceutically acceptable form thereof, which treats the pain in question. By "pain treatment", we mean a clinical application or administration to a subject that can reduce the subject's pain sensation by at least 10%. Preferably, it reduces the pain sensation by 15%, or more preferably, by 20%. In other embodiments, "pain treatment" may also refer to a clinical application or administration to prevent, mitigate, reduce, and/or delay of an expected pain or an increased pain in a subject.

To determine the pain treating effective amount of the compound to be administered in the treatment of pain, the physician may, for example, evaluate the effects of a given chimeric toxin in the patient by incrementally increasing the dosage until the desired symptomatic relief level is achieved. A continuing or repeated dose regimen may also be used to achieve or maintain the desired result. Other techniques known in the art may also be followed in determining the effective amount range for the desired result.

Considering that once the compound is uptaken into the cells, the effective amount could become ligand dependent. Thus, one may determine an effective amount based on the amount of the ligand that is required to reach the desired result. In one embodiment, the effective amount is in the range of 5 to 10000 U of the ligand, which is typically delivered in a volume of 1 mL. In another embodiments, the formulation is delivered in an effective amount in the range of 0.005 to 1000 micrograms of the ligand. Preferably, the formulation is delivered in an effective amount of 0.5 micrograms of the ligand.

Administration of the formulation can be carried out by any operations known in the art. The administering location can, for example, be an intramuscular, intravenous or intraneural, an intrathecal or intradural, or other locations which correspond to administration into a muscle, a vein or the nervous system. Preferably, the formulation is administrated by injection into lumbar intrathecal puncture space. Typically, such intrathecal administration can be carried out by using a lumbar puncture needle.

Pain treated in accordance with the method of the present invention can be any type of acute or chronic pain. Examples of pain include, but not limited to inflammatory pain, musculoskeletal pain, bony pain, lumbosacral pain, neck or upper back pain, visceral pain, somatic pain, neuropathic pain, cancer pain, pain caused by injury or surgery such as burn pain, or headaches such as migraines or tension headaches, or combinations of these pains. One skilled in the art would recognize that these pains may overlap one another. For example, a pain caused by inflammation may also be visceral or musculoskeletal in nature. In one embodiment, the pain is a chronic pain arising from cutaneous injury and inflammation, musculoskeletal injury and inflammation, visceral inflammation or injury, or peripheral nerve injury as caused by chemicals, metabolic disease, or physical injury.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In one embodiment, the pain transmission regulated by the chimeric toxin and the methods of the present invention can be long-lasting and/or stable and/or reversible.

By "long-lasting" or "stable" pain regulation, we mean that a prolonged relief, decreasing or diminishment of pain for periods far in excess of the courses where the patient has not received any treatment or has been treated with the compounds or methods different from those disclosed in the present invention.

In one embodiment, the term "long-lasting" refers to a period of time of at least about 2 hours, 4 hours, 6 hours, 8 hours, 12 hours, one day, two days, one week, two weeks or about 30 days. All possible ranges within this range are also considered to be part of the invention (e.g., about 12 hours to about 48 hours; about 24 hours to about 72 hours; about 3 days to about 5 days; about 5 days to about 7 days; about 7 days to about 10 days).

The term "stable" is used herein also to describe the stability of the compounds, which means that the compounds possess stability and maintain their integrity such as the chemical, physical, biological or pharmaceutical activities for a sufficient period of time to be useful for the desired purposes, including, but not limited to, therapeutic administration to a subject.

For example, in one embodiment, the compounds are stable if at least 50%, 60%, 70%, 80%, 90% or 95% of the integrity and/or stability are retained for a period of time of at least about 2 hours, 4 hours, 6 hours, 8 hours, 12 hours, one day, two days, one week, two weeks or about 30 days.

By "reversible," we mean being in a condition where the regulation of pain by the compounds or methods of present invention can change phases or physical or biological state in response to an internal or external stimuli. The term "reversible" may also mean that the phase of the compounds or pain regulation returns toward its initial phase or physical or biological state at some time after removal of the internal or external stimuli.

It should be understood that the present invention has been described above with respect to its preferred embodiments. Other forms of this concept are also intended to be within the scope of the claims.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Recombinant Synthesis in *E. coli*

In this Example, the sP-LC construct is created by expression of recombinant LC in *E. coli*, with sequence encoding sP/DAMGO fused to the LC via a thrombin cleavable disulfide linker (Baldwin, et al., 2004; Chen, et al., 2012). This will create an sP or DAMGO-LC construct linked by a single disulfide bond, which can be cleaved inside the endosome after endocytosis, releasing LC into cell. This strategy is similar to the strategy for sP-saporin, leading to cellular intake of saporin (Wiley, et al., 1997; Wiley, et al., 2003).

In addition, a construct directly fusing the sP or DAMGO sequence to the LC without a disulfide-linker is also created, to determine whether this simpler construct will be equally internalized. Purification and thrombin cleavage will be performed as described ( 2012). The resulting construct (FIG. 4) will be analyzed by SDS-PAGE gel and immunoblot analyses, alongside BoNT holotoxin. BoNT serotypes are routinely purified in the Johnson lab. Purity is assessed by SDS-PAGE analysis and the absence of toxicity confirmed by mouse bioassay (Schantz, et al., 1978; Hatheway, et al., 1988). LC activity will be confirmed by in vitro endopeptidase assays (BoTest; Biosentinel, Madison, Wis.). Treatment with a reducing agent (dithiothreitol) may be necessary to achieve function of LC.

Example 2

Chemical Synthesis

This Example provides an alternative way to construct sP-LC, in which the synthesized sP (Bio-Synthesis, Lewisville, Tex.) can also be chemically linked to recombinantly expressed LC by disulfide bonding without affecting their function (Anton, et al., 1991, Wiley, et al., 1997; Wiley, et al., 2003; Wiley, et al., 2007). Specifically, two strategies are described, both of which have been used to make similar constructs of sP-saporin.

In the first strategy, BoNT-LC is derivatized with SPDP (N-succinimidyl-3-[2-pyridyldithio]propionate), and mono-derivatized LC is selected as described for similar saporin derivatives. (Lappi, et al., 1993). A 5-fold excess of modified sP and DAMGO peptides containing cysteine at the C-terminal end and a 6 glycine linker is added to the LC derivative to allow for conjugation, and excess sP or DAMGO will be removed by dialysis.

In the second strategy, BoNT LC construct is extended to contain the cysteine 430 at the C-terminus. LC construct is treated with a reducing agent such as dithiothreitol to break up dimers, and dialyzed into a buffer that will maintain the free sulfhydryl group of the cysteine (e.g. containing 1-10 mM (ethylenedinitrilo)-tetraacetic acid). LC construct is reacted with sP or DAMGO constructs containing a cysteine or a cysteine modified with a pyridyl thione group at the N-terminal end, as above. The resulting conjugates is analyzed by SDS-PAGE and Western blot analysis (as described above) to confirm that a single molecule of sP is attached to the LC. LC activity will be confirmed by in vitro endopeptidase assays (BoTest; Biosentinel, Madison, Wis.). Treatment with a reducing agent such as dithiothreitol may be necessary to achieve full function of the LC.

Example 3

Creation of Functional Targeted BoNT LC

The essential deliverable is the LC-peptide constructs (sP-LC; DAMGO-LC). We have two separate rational and robust strategies. The first is expression of constructs based on BoNT/LC (aa 1-425) in *E. coli* (Baldwin, et al., 2004). While full length LC of BoNT undergoes precipitation and autocatalysis (Ahmed, et al., 2001; Ahmed, et al., 2004; DasGupta, et al., 2005), we have shown that a slightly shortened version is catalytically active and stable. It contains a his6-tag for easy purification (Baldwin, et al., 2004). The Johnson lab developed and used this expression system (Baldwin, et al., 2004). Alternatively, the synthesized sP or a similar peptide can be chemically linked to recombinantly expressed LC by disulfide bonding, which in the case of sP-Saporin, did not affect its function (Wiley, et al., 1997; Wiley, et al., 2003; Wiley, et al., 2007). In recent work, we found that such a sP-LC construct can be created by chemical linkage.

Figure 4:
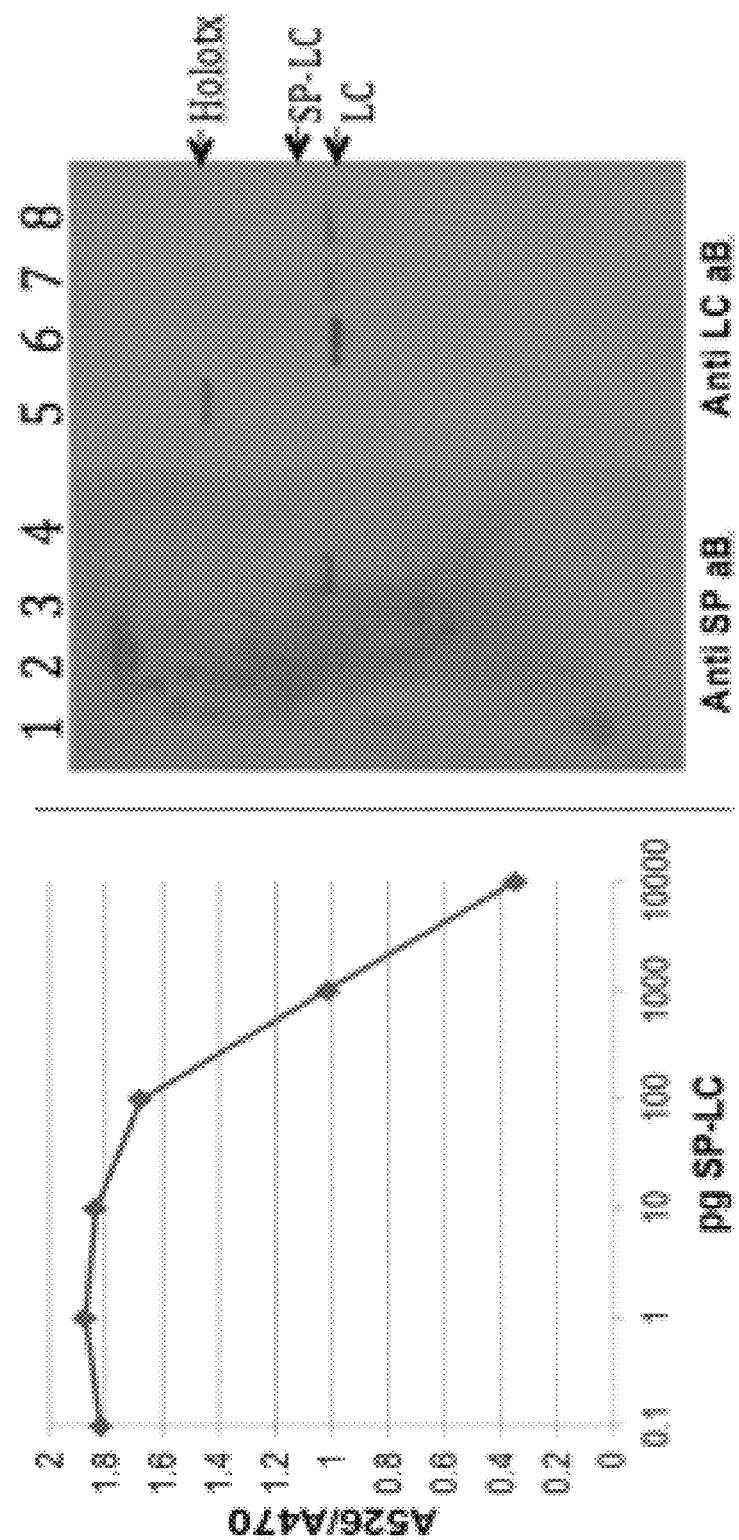
FIG. 4 shows the creation of a functional sP-LC construct: BoNT/A1 holotoxin (Holotx) was loaded on a QAE sephadex column. Column was washed sequentially with equilibrating buffer+0.01 M DTT and then equilibrating buffer+0.1 M DTT+2 M urea. Column incubated overnight to allow for reduction of disulfide bond linking heavy and light chains. Light chain (LC) was eluted in equilibrating buffer+0.01 M DTT+2 M urea, concentrated in a microconcentrator (20 kDa MW cut-off), and applied to a PD10 desalting column to remove DTT. Substance P-SH was added directly to the LC solution from PD10 column. Mixture incubated overnight at 4° C. to allow for disulfide linkage. The sP-LC construct separated from unconjugated sP/sP dimer on PD 10 desalting column. Left: reduced and non-reduced sP-LC construct were analyzed by Western blot alongside BoNT/A holotx using a sP antibody (left 1-4) and a BoN/A LC antibody (right 5-8). The sP-LC construct is recognized by both sP and LC antibodies. sP signal is lost upon reduction. This indicates proper conjugation of sP to the LC. Blot Lanes: 1,5: BoNT/A1; 2,6: BoNT/A1 reduced; 3,7: sP-LC reduced; 4,8: BoNT/A1. Right: sP-LC construct analyzed in vitro using BoTest (BioSentinal), in which LC specifically cleaves a SNAP-25 substrate, leading to a fluorescent energy transfer shift, as depicted by the A526/A470 ratio. The non-reduced construct cleaved SNAP-25 substrate with an EC50 of 500 pg. The small holotoxin contamination in the construct would not be capable of producing such high activity under the non-reducing conditions used in the assay, indicating that enzymatic activity of LC was maintained in the sP-LC construct.

For a 'proof of concept' experiment, the LC and HC of the BoNT/A1 holotoxin were separated and LC linked to a synthetically produced sP peptide containing a glycine linker and C-terminal cysteine for disulfide binding. FIG. 4 shows a Western blot demonstrating that such a construct can be created, and an in vitro endopeptidase assay demonstrating that LC activity is maintained in the sP-LC construct. While this 'proof of concept' experiment was based on separation of HC and LC of the BoNT/A holotoxin, leading to minor holotoxin contamination of the resulting construct, the methods proposed in this project will use recombinant BoNT LC only, thereby preventing functional *botulinum* toxin contamination (FIG. 4).

In order to ensure that the BoNT/A holotoxin contamination of the sP-LC does not interfere, the sP-LC preparation was mixed with an excess of anti-BoNT/A heavy chain specific antibody, which neutralizes the toxins activity. This was confirmed by exposing neuronal cells to the sP-LC/antibody mixture or only the sP-LC. In the presence of antibody, no SNAP-25 cleavage was observed, while cleavage was apparent in the absence of antibody. In addition, a mouse was injected with the same mixtures, and the mouse receiving the sP-LC antibody mixture showed no signs of *botulism*, while the mouse receiving only the sP-LC died of *botulism*. For all following studies, the same sP-LC/antibody mixtures were used.

Example 4

Intrathecal Drug Delivery

An important aspect of this invention is the analysis of the spinal actions vivo on pain behavior of the sP-LC. To accomplish this, mice received percutaneous lumbar intrathecal injections and the effects of the injection on the flinching behavior otherwise produced by the intraplantar injection of formalin was assessed.

In previous work, we have shown that the intrathecal delivery of BoNT will result in a potent suppression of the phase 2, but not phase 1 flinching response otherwise evoked by the injection of formalin into the paw. This effect is believed to reflect the ability of such intrathecal injection to block the release of transmitters from the primary sensory afferents. (Huang, et al., 2011) It is considered likely that the phase 2 of the formalin represents a facilitated state initiated in part by the release of the neuropeptide sP which then binds to neurokinin 1 receptors that are present on second order projection neurons (Todd, et al., 2002). Importantly, the NK1 receptor is a G protein coupled receptor that shows internalization when occupied by its ligand. In the present work we sought to determine if the light chain of a BoNT (the active cleaving component) coupled to substance P would be taken up into the second order pain transmitting neurons and block its ability to transmit the afferent evoked in-put. As the internalization would be limited to NK1 bearing neurons the *botulinum* effect would be selective only for that limited class of neurons.

Male C57 Cl6 mice were lightly anesthetized. Vehicle or sP-LC BoNT-A was then injected IT (0.55 µg/10 µL), 24 hours prior to the injection of 20 µL of 2.5% Formalin injected SQ into the paw. Flinching was counted by an automated flinch counting systems. The same mice were perfused 2 hr after the intraplantar formalin. Spinal cords were dissected sectioned and stained for cFOS immunoreactivity.

Figure 5A:
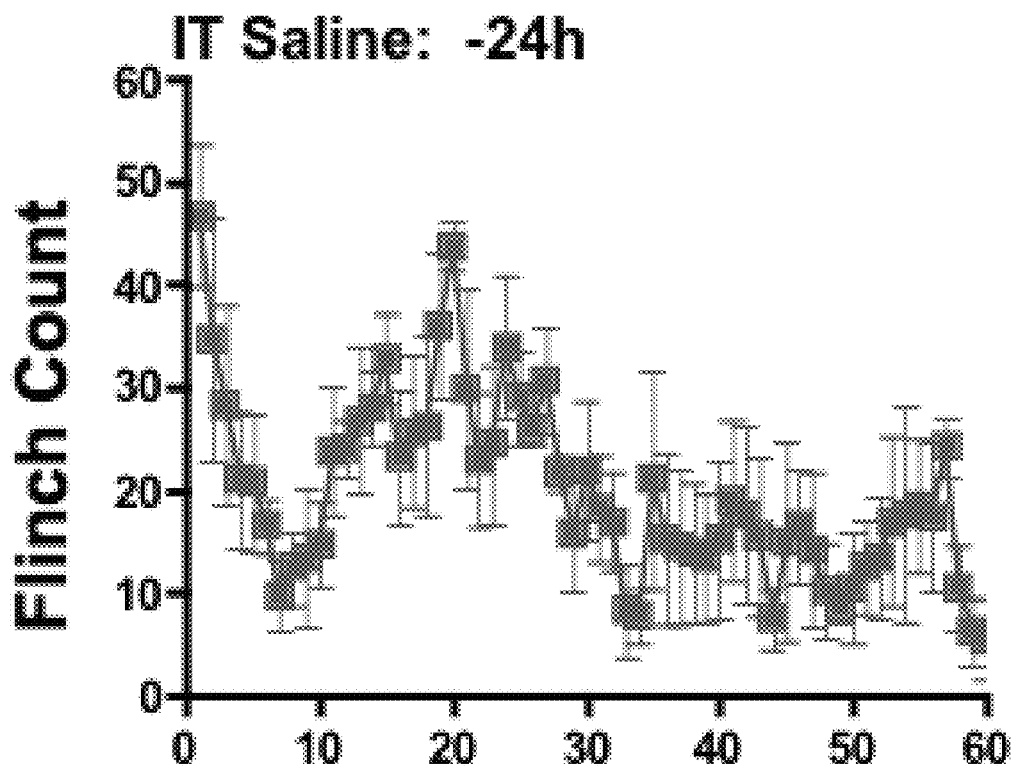
Figure 5B:
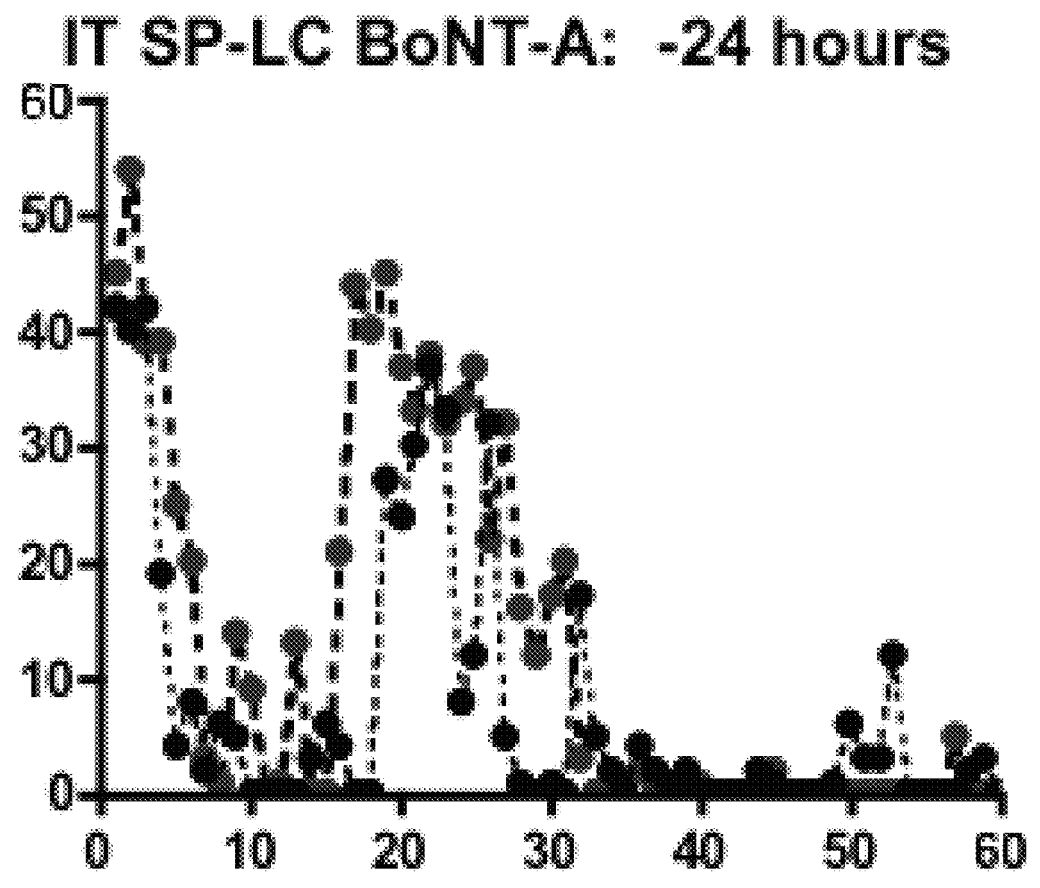
Figure 5C:
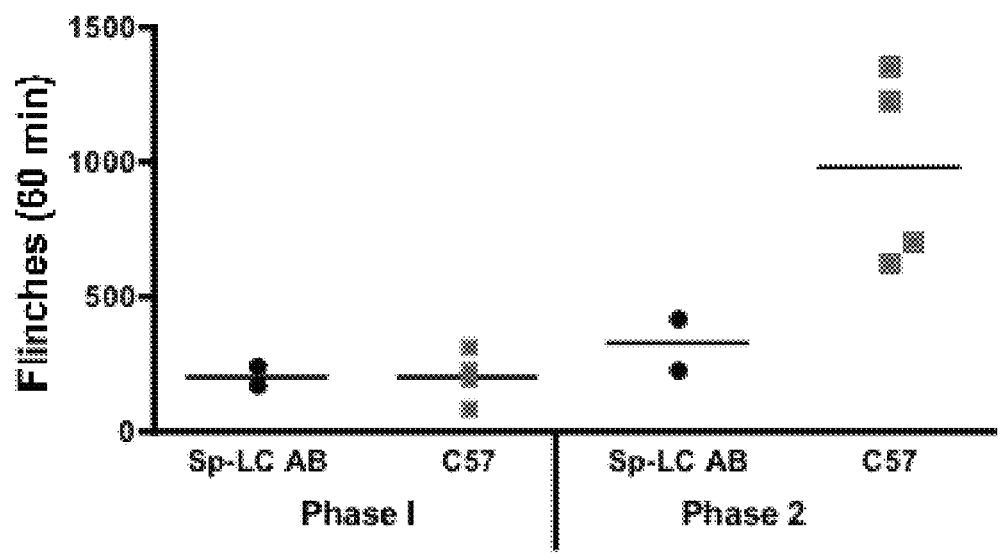

FIG. 5 (top) displays the biphasic flinching evoked over 60 min by intraplantar formalin in 4 control mice. In contrast, intrathecal sP-LC BoNT-A in mice resulted in prominent reduction in the phase 2, but not the phase 1 formalin evoked flinching. FIG. 5 (bottom) summarizes the data by presenting the cumulative phase 1 and phase 2 flinching scores for the 60 min test interval. Again while there was no difference between the treatment group in phase 1, both of the mice receiving the sP-LC were less than 30% of the control animal flinching scores otherwise evoked by the formalin.

Figure 6A:
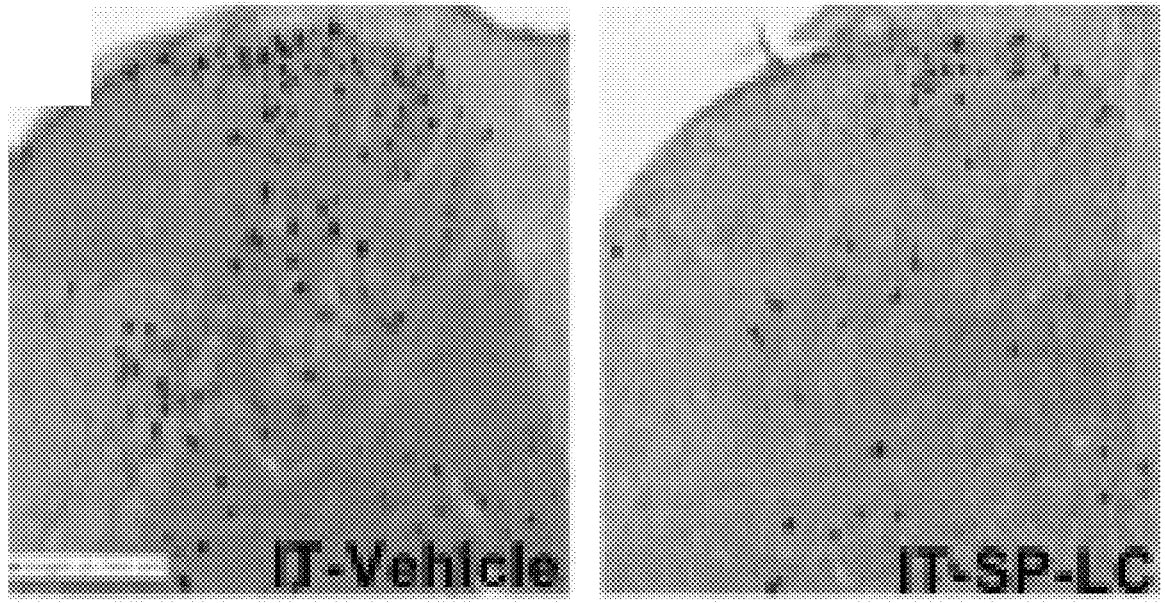
FIG. 6A-B shows that the staining for cFOS revealed reliable increases in cFOS(+) cells in the dorsal horn ipsilateral to the formalin injection. A. cFOS(+) cells in ipsilateral dorsal horn after IPLT formalin in mice receiving IT vehicle (left) or IT sP-LC (right) B. cFOS cell counts in superficial (Lam 1-2) and deep (Lam 3-5) ipsilateral dorsal horn. Note reduction in cFOS counts in dorsal horn of IT-sP-LC mice. as compared to vehicle.
Figure 6B:
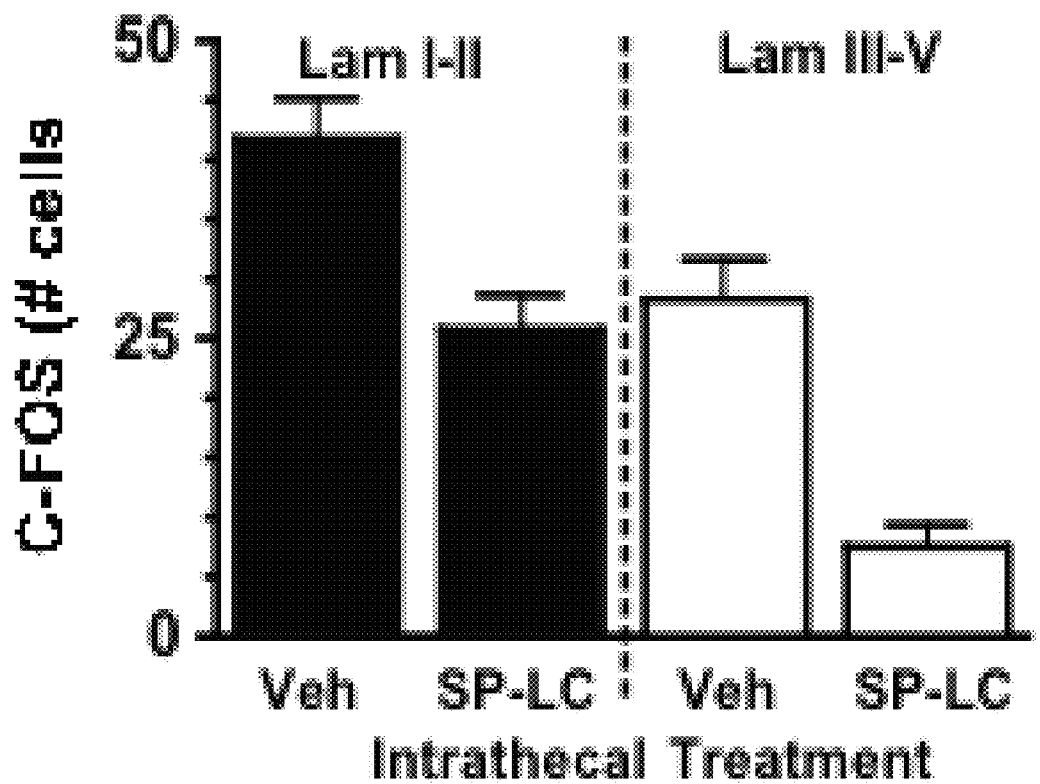

Staining for cFOS revealed reliable increases in cFOS(+) cells in the dorsal horn ipsilateral to the formalin injection (FIG. 6). In the two mice treated 24 hrs in advance with IT-sP-LC, the formalin evoked increase was blocked suggesting that there was a block of the formalin initiated afferent evoked excitation of dorsal horn neurons. These results suggest that intrathecally delivered sP-LC at doses that were not impairing of motor function resulted in a powerful suppression of pain behavior and a suppression of spinal neuronal markers (cFOS) normally activated by the formalin stimulus.

Example 5

Stability of sP-LC Construct

It is known that the BoNT/A LC undergoes autocatalytic activity if not linked to the HC. Previously, whether this autocatalysis also occurs after linkage of the LC to sP was unknown. Two different batches of the construct produced as above appeared unstable after over 2 weeks of storage as indicated by repeat SDS-PAGE analysis, Western analysis, and functional studies in animals, even if stored in 40% glycerol at −20° C. This invention utilizes a stable BoNT/A LC that lacks the autocatalytic susceptible region of BoNT and has been optimized for solubility and stability while maintaining all catalytic function to create stable products that can be consistently produced.

A recent publication (Mustafa, et al., 2013) described a similar construct of the BoNT/A LC linked to sP. It was reported in that publication that a BoNT/A LC (aa 1-437) was used, which is longer than the light chain (aa 1-425) that is preferred in the present invention. The longer BoNA/A LC (aa 1-437) which has previously been shown to result in lower solubility. In addition, while the results presented in the publication indicate the potential for entry into NK1-receptor bearing cells and a pain block response, the presented data are not convincing for a number of reasons. For example, stability of the construct is not shown in this publication. The authors showed the absence of SNAP-25 by Western blot using an unspecified antibody, but the proper way to show SNAP-25 cleavage would be to use an antibody that detects both cleaved and uncleaved SNAP-25, or specifically detects cleaved SNAP-25. The ICC data are lacking control, and show only one cell for each, sP-LC and LC treated cells.

REFERENCES

Ahmed, et al., Enzymatic autocatalysis of *botulinum* A neurotoxin light chain. *J Protein Chem.* 2001 April; 20(3): 221-231.

Ahmed, et al., Factors affecting autocatalysis of *botulinum* A neurotoxin light chain. *Protein J.* 2004 October; 23(7): 445-451.

Anton, et al., Development of a biotinylated analog of substance P for use as a receptor probe. *Lab Invest.* 1991 May; 64(5): 703-708.

Baldwin, et al., The C-terminus of *botulinum* neurotoxin type A light chain contributes to solubility, catalysis, and stability. *Protein Expr Pur* 2004 September; 37(1): 187-195.

Belanger, et al., Expression of calcitonin gene-related peptide, substance P and protein kinase C in cultured dorsal root ganglion neurons following chronic exposure to mu, delta and kappa opiates. *Neuroscience.* 2002, 115(2):441-53.

Chen, et al., Design of an in vivo cleavable disulfide linker in recombinant fusion proteins. *BioTechniques,* 2010. 49(1): p. 513-8.

Dasgupta, et al. *Botulinum* neurotoxin\ types A, B, and E: Fragmentations by autoproteolysis and other mechanisms including by O-phenanthroline-dithiothreitol, and association of the dinucleotides NAD(+)/NADH with the heavy chain of the three neurotoxins. *Protein J.* 2005 August; 24(6): 337-368.

Dorner, et al., Complexity of *botulinum* neurotoxins: challenges for detection technology. *Curr Top Microbiol Immunol.* 2013, 364:219-55.

Huang, et al., Spinal *botulinum* neurotoxin B: effects on afferent transmitter release and nociceptive processing. *PLoS One.* 2011 Apr. 29; 6(4):e19126. Erratum in: PLoS One. 2011; 6(8).

Hatheway, C L., *Botulism.* In: Balows A, Hausler W H, Ohashi M, Turano M A, editors. Laboratory diagnosis of infectious diseases: principles and practice. New York: Springer-Verlag; 1988. p. 111-133.

Hill, et al., Genetic Diversity Within *Clostridium botulinum* Serotypes, Botulinum Neurotoxin Gene Clusters and Toxin Subtypes. *Curr Top Microbiol Immunol.* 2013, 364:1-20.

King, et al., Evolution of key cell signaling and adhesion protein families predates animal origins. *Science* 2003, 301 (5631): 361-3

Lappi, et al., Reducing the heterogeneity of chemically conjugated targeted toxins: Homogeneous basic FGF-saporin. *Anal Biochem.* 1993 Aug. 1; 212(2): 446-451.

Mustafa, et al., Anti-nociceptive effect of a conjugate of substance P and light chain of *botulinum* neurotoxin type A. *Pain,* 2013, 2547-2553.

Schantz, E. J. and Kautter, D. A., Standardized assay for *clostridium botulinum* toxins. *Journal of the Association of Official Analytical Chemists.* 1978; 61: 96-99.

Todd, et al., Projection neurons in lamina I of rat spinal cord with the neurokinin 1 receptor are selectively innervated by substance p-containing afferents and respond to noxious stimulation. *J Neurosci.* 2002 May 15; 22(10):4103-13.

Wiley, et al., Anti-nociceptive effects of selectively destroying substance P receptor-expressing dorsal horn neurons using [Sar9,met(O2)11]-substance P-saporin: Behavioral and anatomical analyses. *Neuroscience.* 2007 May 25; 146(3): 1333-1345.

Wiley, et al., Destruction of neurokinin-1 receptor expressing cells in vitro and in vivo using substance P-saporin in rats. Neurosci Lett. 1997 Jul. 18; 230(2): 97-100.

Wiley, et al., Targeted toxins in pain. *Adv Drug Deliv Rev.* 2003 Aug. 28; 55(8): 1043-1054.

Yaksh, et al., An automated flinch detecting system for use in the formalin nociceptive bioassay. *J Appl Physiol.* 2001 June; 90(6):2386-402.

We claim:

1. A chimeric toxin comprising
   (a) a peptide ligand specifically targeting neurons involved in pain processing; wherein the ligand is Substance P (SEQ ID NO:1), and
   (b) a clostridial neurotoxin light chain, wherein the light chain is *botulinum* toxin type A light chain,
wherein the ligand is linked to the light chain to form a chimeric toxin, and wherein the chimeric toxin does not comprise a translocation domain.

2. The toxin of claim 1, wherein the link is a covalent bond.

3. The toxin of claim 1, wherein the covalent bond comprises a disulfide linker.

4. A pharmaceutical formulation comprising
   (a) a therapeutically effective amount of a chimeric toxin comprising
      (i) a peptide ligand specifically targeting neurons involved in pain processing, wherein the ligand is substance P (SEQ ID NO:1); and
      (ii) a clostridial neurotoxin light chain, wherein the light chain is type A light chain,
   wherein the ligand is linked to the light chain to form a chimeric toxin, and wherein the chimeric toxin does not comprise a translocation domain;
   and
   (b) a pharmaceutically acceptable carrier.

* * * * *

SEQUENCE LISTING

<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Synthetic - substance P
<220> FEATURE:
<221> NAME/KEY: MOD_RES
<222> LOCATION: (11)..(11)
<223> OTHER INFORMATION: AMIDATION

<400> SEQUENCE: 1

Arg Pro Lys Pro Gln Gln Phe Phe Gly Leu Met
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Synthetic

<400> SEQUENCE: 2

Met Leu Gly Phe Phe Gln Gln Pro Lys Pro Arg Gly Gly Gly Gly Gly
1               5                   10                  15

Gly Tyr Cys Ser Ser
            20

<210> SEQ ID NO 3
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: D-ALANINE
<220> FEATURE:
<221> NAME/KEY: MOD_RES
<222> LOCATION: (4)..(4)
<223> OTHER INFORMATION: N-METHYLATION
<220> FEATURE:
<221> NAME/KEY: MOD_RES
<222> LOCATION: (5)..(5)
<223> OTHER INFORMATION: GLY-ol

<400> SEQUENCE: 3

Tyr Ala Gly Phe Gly Gly Gly Gly Gly Gly Tyr Cys Ser Ser
1               5                   10                  15